(12) United States Patent
Yoneda et al.

(10) Patent No.: US 6,258,591 B1
(45) Date of Patent: Jul. 10, 2001

(54) ONE-PACK PREPARATION FOR DISINFECTION, NEUTRALIZATION AND CLEANING OF CONTACT LENSES AND METHOD OF DISINFECTION, NEUTRALIZATION AND CLEANING

(75) Inventors: Toyoaki Yoneda, Takarazuka; Takashi Fujii, Kinosaki-gun; Mika Morita, Toyooka; Takeshi Ohnuma, Machida; Hiroshi Tanouchi, Takarazuka; Shigeru Nakamura, Toyooka, all of (JP)

(73) Assignee: Ophtecs Corporation, Osaka (JP)

(*) Notice: Subject to any disclaimer, the term of this patent is extended or adjusted under 35 U.S.C. 154(b) by 19 days.

(21) Appl. No.: 09/194,779

(22) PCT Filed: Apr. 3, 1997

(86) PCT No.: PCT/JP97/01150

§ 371 Date: Dec. 3, 1998

§ 102(e) Date: Dec. 3, 1998

(87) PCT Pub. No.: WO98/43683

PCT Pub. Date: Oct. 8, 1998

(51) Int. Cl.[7] .................................................... C12S 9/00
(52) U.S. Cl. ......................... 435/264; 422/37; 510/114; 514/840; 134/901
(58) Field of Search ................................. 435/264, 262; 422/37; 510/112–115; 134/27, 901; 514/840

(56) References Cited

U.S. PATENT DOCUMENTS

| | | |
|---|---|---|
| 3,911,107 | 10/1975 | Krezanoski . |
| 4,312,833 | 1/1982 | Clough et al. . |
| 4,937,072 * | 6/1990 | Kessler et al. . |
| 4,976,921 | 12/1990 | Itagaki et al. . |
| 5,169,455 * | 12/1992 | Kessler . |
| 5,356,555 * | 10/1994 | Huth et al. . |
| 5,460,658 * | 10/1995 | Nakagawa et al. . |
| 5,462,713 * | 10/1995 | Schlitzer et al. . |

FOREIGN PATENT DOCUMENTS

| | | |
|---|---|---|
| 1604020 | 12/1981 | (GB) . |
| 50-157516 | 12/1975 | (JP) . |
| 1160902 | 6/1989 | (JP) . |
| 6102474 | 4/1994 | (JP) . |
| 8224288 | 9/1996 | (JP) . |
| 8327956 | 12/1996 | (JP) . |
| WO96/00590 | 1/1996 | (WO) . |
| WO96/00591 | 1/1996 | (WO) . |

OTHER PUBLICATIONS

C.D. Shively, et al., "Hydrophilic Flexible Lens Cleaning and Chemical Disinfection Systems", Contacto, May 1975, pp. 33–37 (1975).

R. Kono, et al., "Antiviral Effect of a Disinfectant (Pliacid/NutraFlow System) for Soft Contact Lenses", Bull. Jap. Contact Lens Soc., No. 23, pp. 150–154 (1981).

T. Matsumoto, et al., "A New Germicidal Agent of Soft Contact Lenses", Bull. Jap. Contact Lens Soc., No. 20, pp. 96–101 (1978).

H. Conn, et al., "Iodine Disinfection of Hydrophilic Contact Lenses", Annals Opthamology, Mar. 1981, pp. 361–364 (1981).

J.H. Draize, et al., "Methods for the Study of Irritation and Toxicity of Substances Applied Topically to the Skin and Mucous Membranes", pp. 377–390 (1944).

* cited by examiner

*Primary Examiner*—William H. Beisner

(57) ABSTRACT

The present invention provides a combined formulation for disinfecting, neutralizing and cleaning a soft contact lens and a method using the same easily, efficiently and safely. The formulation is a one-solution type of combined formulation for disinfecting, neutralizing and cleaning a soft contact lens, which includes a first formulation that contains an iodine-based disinfectant and a proteolytic enzyme and a second formulation that contains a reducing and a foaming agent treated with a delayed release coating, and which contains a nonionic surfactant in at least one of the first and second formulations. A stained soft contact lens can be disinfected, neutralized and cleaned easily by holding it in an aqueous solution colored yellow or brown by iodine molecules and removing it from the aqueous solution after the solution becomes almost colorless.

24 Claims, No Drawings

ONE-PACK PREPARATION FOR DISINFECTION, NEUTRALIZATION AND CLEANING OF CONTACT LENSES AND METHOD OF DISINFECTION, NEUTRALIZATION AND CLEANING

FIELD OF THE INVENTION

This invention relates to a one-solution type of combined formulation for disinfecting, neutralizing and cleaning contact lenses and a method of caring for contact lenses using the same. More specifically, it relates to a one-solution type of combinated formulation suitable for disinfecting, neutralizing and cleaning soiled contact lenses quickly and simply, and a method for caring for a contact lenses using the same.

PRIOR ART

Methods that have been currently used for disinfecting soft contact lenses are roughly divided into disinfection by boiling and disinfection by chemicals. Although disinfection by boiling is substantially effective for the disinfection of all kinds of microorganisms such as bacteria, viruses and molds, it may cause a lens to become white turbidity due to the denaturation and coagulation of protein or other substances adhering to a soft contact lens by heat or the deformation and discoloration of a lens by long-term repeated heating. This method has such inconvenience that it cannot be used without a power source.

A large number of methods for disinfection by chemicals have been also known, and some of 3% hydrogen peroxide and biguanide-based antiseptic solutions have a low sterilizing effect according to types of microorganisms. When misused, they act as an excessively strong irritant to the cornea epithelium and conjunctiva and may cause a disorder of the cornea.

Of various halogen-based disinfectants, iodine-based disinfectants are excellent chemical disinfectants in terms of sterilizing effect and safety to eyes. Examples of disinfection using these iodine-based disinfectants are described in the specification of UK Patent No. 1,604,020, the specification of U.S. Pat. No. 4,312,833, Contacto, pp. 33 to 37 (1975), the Bulletin No. 23 of the Japan Contact Lens Society, pp. 150 to 154 (1981) and the Bulletin No. 20 of the Japan Contact Lens Society, pp. 96 to 101 (1978). However, in these methods, the removal and neutralization of the residual disinfectant after disinfection using an iodine-based disinfectant are carried out by the self-sublimation of iodine or using a weak reducer. Therefore, the removal of active iodine takes a long time and the neutralization may be incomplete. As a result, a soft contact lens may be changed color as the iodine agent is adsorbed to the matrix of the lens and may be deformed or deteriorated by the reaction between iodine and the lens material.

Further, though the iodine formulation is relatively safe to eyes, when it is adsorbed and accumulated in a lens without being completely neutralized, an iodine-based chemical is gradually released while the lens is worn and may inflame the eyes of an allergic person or cause a disorder of the cornea, as described in Annals Ophthalmology, pp. 361 to 364 (1981). WO 96/00590 and WO 96/00591 disclose a method for disinfecting contact lens and subsequent reduction, wherein the lens are contacted with a solution combinated with a reducing solution and an excess amount of iodine formulation than the required amount for oxidizing a contained reducer, and further a reducer is added to reduce the residual iodine formulation. In addition, of cares of a soft contact lens, it is important to remove protein or lipid adhering to a lens, and a cleaning agent is required for this purpose. However, there has not been yet known a one-solution type of combinated formulation comprising an iodine disinfectant, neutralizer, proteolytic enzyme and surfactant.

SUMMARY OF THE INVENTION

It is an object of the present invention to provide a one-solution type of combinated formulation for carrying out disinfection, neutralization and cleaning in one solution.

It is another object of the present invention to provide a one-solution type of combinated formulation suitable for disinfecting, neutralizing and cleaning a soiled contact lens quickly and easily.

It is still another object of the present invention to provide a one-solution type of combinated formulation for disinfecting, neutralizing and cleaning a soft contact lens easily, which comprises not only of an iodine disinfectant exhibiting a strong sterilizing effect but also relatively high safety to improve the defect of a formulation using a neutralization method of the prior art by combinating two other formulations.

It is still another object of the present invention to provide a method for cleaning a soiled contact lens quickly and easily using the one-solution type of combinated formulation of the present invention.

Other objects and advantages of the present invention will become apparent from the following description.

According to the present invention, firstly, the above objects and advantages of the present invention can be attained by a one-solution type of combinated formulation for disinfecting, neutralizing and cleaning a contact lens, which comprises (A) the first formulation containing an iodine-based disinfectant and a proteolytic enzyme and (B) the second formulation containing a reducer and a foaming agent and having a delayed release coating, and containing a nonionic surfactant in at least one of the first and second formulations.

The one-solution type of combinated formulation of the present invention comprises the first formulation (A) and the second formulation (B) at least one of which contains a nonionic surfactant.

The first formulation contains an iodine-based disinfectant and a proteolytic enzyme, and a nonionic surfactant as the case may be.

The iodine-based disinfectant advantageously used in the present invention is conventionally well-known as povidone iodine or polyvinly alcohol iodine wherein iodine molecules ($I_2$) are included in macromolecule such as polyvinyl pyrrolidone (PVP) or polyvinyl alcohol (PVA). These macromolecule-coupled iodine agents are extremely excellent disinfectants which (1) are water-soluble, (2) stabilize subliming and unstable iodine molecules in a solid state, and (3) reduce toxicity, as compared with free iodine agents, and which have strong bactericidal action equal to that of free iodine agents. Namely, the disinfectants have a wide range of antibacterial spectra against bacteria, antibiotic resistant germs, molds, viruses and the like.

The proteolytic enzyme advantageously used in the present invention must retain sufficient cleaning power for a lens soiled with protein in the presence of the iodine disinfectant which is a strong oxidant. Since a sulfur group, that is, particularly sulfur atoms such as a thiol group or dithio group, are readily oxidized by an iodine compound, the activity of enzymes having a large number of these sulfur groups, such as papain, bromelain, ficin, pancreatin and cathepsin is greatly reduced by the presence of the iodine disinfectants. Therefore, they cannot be recommended as a preferred enzyme cleaning agent in the present invention.

Experiments have been conducted on stability using various enzymes under the presence of the iodine formulation. As a result, it has been found that proteolytic enzymes produced by bacillus bacteria and enzymes derived from animal pancreases are relatively stable.

Proteolytic enzymes available on the market include Bioprase, Biotamilase (of Nagase Biochemicals Ltd.), Protease N "Amano" (of Amano Pharmaceutical Co., Ltd.), Subtilisin A, Alcarase, Esperase, Trypsin, Chymotrypsin (of Novo Nordisk Bioindustry Ltd.) and the like. A suitable one is selected out of these.

The first formulation contains an iodine-based disinfectant preferably in an amount of 0.01 to 50 wt %, more preferably 0.1 to 15 wt %, based on the first formulation. When the first formulation is dissolved in an aqueous solution as the combinated formulation of the present invention, the iodine-based disinfectant is contained in the aqueous solution preferably in an amount of 1 to 5,000 ppm, more preferably 10 to 1,500 ppm in terms of the concentration of effective iodine. If the concentration is less than 1 ppm, the disinfecting power of the disinfectant will lower. On the other hand, if the concentration is more than 5,000 ppm, the disinfectant will have a prolonged neutralization time and affect a lens, thereby making it difficult to handle.

And the first formulation contains a proteolytic enzyme preferably in an amount of 0.01 to 50 wt %, more preferably 0.1 to 20 wt % based on the first formulation. When the first formulation is dissolved in an aqueous solution as the combinated formulation of the present invention, the concentration of the proteolytic enzyme contained in the aqueous solution, which is suitably determined according to its cleaning effect and enzyme activity, is preferably 0.0001 to 0.5 wt %.

Preferred examples of the nonionic surfactant which the first formulation may contain, include Poloxamer (polyoxyethylene, polyoxypropylene block polymer), Poloxamine (polyoxyethylene, polyoxypropylene block polymer of ethylene diamine), Polysorbate 80 (polyoxyethylene 20 sorbitan monooleate), Polyoxyl 40 (polyethylene glycol monostearate) Stearate and Polyoxyethylene Hydrogenated Castor Oil 60.

The nonionic surfactant is contained in the first formulation preferably in an amount of 0.01 to 50 wt %, more preferably 0.1 to 20 wt% based on the first formulation. When the combinated formulation of the present invention is dissolved in an aqueous solution, the nonionic surfactant is contained in the aqueous solution preferably in an amount of 0.0001 to 0.5 wt %, more preferably 0.001 to 0.2 wt %.

Meanwhile, the second formulation contains a sulfur-containing reducer and a foaming agent, and a nonionic surfactant as required, and has a delayed release coating.

As the reducer, may be used the known powerful reducers for iodine and halogenating agents. Sodium sulfite, sodium hydrogen sulfite, sodium thiosulfate, ascorbic acid and sodium ascorbate are particularly preferred because they effectively reduce iodine molecules remaining in a soft contact lens after disinfection.

The reducer is contained preferably in an amount of 0.01 to 50 wt %, more preferably 0.1 to 20 wt % based on the second formulation. When the second formulation is dissolved in purified water as the combinated formulation of the present invention, the reducer eventually reacts with an iodine-based disinfectant for reduction.

In addition the foaming agent is preferably sodium bicarbonate or sodium carbonate, for example.

The foaming agent is contained preferably in an amount of 1 to 80 wt %, more preferably 10 to 60 wt % based on the second formulation.

Further, examples of the nonionic surfactant which the second formulation may contain, are the same as those listed for the first formulation.

The second formulation can also contain a nonionic surfactant in the same amount as that of the first formulation.

The second formulation has a delayed release coating. The reason for this is as follows.

The aqueous solution of iodine molecules is colored dark brown to yellow according to its concentration, and iodine is easily adhered to an organic compound as is evident from the fact that it is used as a colorant for thin-layer chromatography for silica gel or alumina. Since a soft contact lens to be disinfected is made from a polymer of an organic compound such as a methacrylic acid derivative, acrylamide derivative or N-vinyl pyrrolidone, iodine molecules are easily adhered to the matrix of a lens at the time of disinfection, whereby the lens is colored yellow or brown. When this state lasts long, it may exert such influences as the denaturation and deterioration of the lens material. When the iodine molecules are reduced by the reducer after disinfection, they are converted into iodo anion ($I^-$), which is colorless and safe and has almost no adsorption power to the lens matrix.

Therefore, it is necessary to reduce the residual excess iodine molecules by the reducer as soon as disinfection is effectively carried out with iodine. For this purpose, the second formulation has a delayed release coating to release the reducer or the like after the contact lens is disinfected by the first formulation.

In other words, merely by holding a soiled lens in an aqueous solution containing the first formulation and the second formulation, the contact lens is first disinfected and cleaned by the first formulation, continuous dissolution of the delayed released coating of the second formulation is completed when the disinfection is almost completed, and finally the residual excess iodine molecules are reduced (neutralized) by the reducer contained in the second formulation. The foaming agent contained in the second formulation assists this reduction reaction effectively and smoothly.

Preferred examples of the delayed release coating used in the present invention include chemically modified celluloses and gelatins. Of these, hydroxypropylcellulose (HPC), hydroxypropylmethylcellulose (HPMC) and hydroxyethylcellulose (HEC) are more preferred.

The delayed release coating is preferably designed to start foaming in 1 to 10 minutes.

In other words, as for the disinfection and cleaning of a contact lens by the first formulation, that is, disinfection by an iodine-based disinfectant and cleaning by a proteolytic enzyme, since the disinfection time is suitably 1 to 10 minutes for carrying out enough disinfection due to ensuring enough cleaning by suppressing the deactivation of the proteolytic enzyme, it is desirable that the effective components of the second formulation are set to be active after disinfection and cleaning by the first formulation.

Therefore, the first formulation is preferably in a powdery or granular form and the second formulation is in the form of a tablet or capsule, or the second formulation forms a center portion and the first formulation covers the center portion as an outer layer (such as a nucleated tablet), or the first and second formulations are in such a form that they are placed side by side. In the latter two forms, it is possible to prevent an involuntary failure to add one of the formulations into a solution.

Therefore, according to the present invention, secondly, there is also provided a method for disinfecting, neutralizing and cleaning a contact lens, which comprises the steps of holding a soiled contact lens in a yellow or brown aqueous solution containing the one-solution type of combinated formulation of the present invention and removing the contact lens from the aqueous solution after the aqueous solution becomes almost colorless.

The aqueous solution containing the one-solution type of combinated formulation can contain a isotonicity, buffer and chelating agent. The aqueous solution is preferably prepared, for example, by dissolving at least one isotonicity selected from the group consisting of sodium chloride and potassium chloride, at least one buffer selected from the group consisting of phosphates, boric acid and borates, and a chelating agent selected from the group consisting of ethylenediamine disodium tetraacetate (EDTA·2Na) and ethylenediamine dipotassium tetraacetate in purified water. As this aqueous solution can be used as a lens rinsing solution after used to disinfect and clean a soft contact lens, it is desired that the isotonicity and pH of the solution are equal to those of human tears.

The method for disinfecting, neutralizing and cleaning of the present invention can be applied to all of known hydrous soft contact lenses. Stated more specifically, a lens is held in a basket fixed to the cap of a capped vial after the vial is filled with an aqueous solution, the first and second formulations are added into the aqueous solution at the same time, the cap having the lens fixed in the basket is closed, and then the vial is shaken several times and allowed to stand. First of all, the disinfectant and cleaning agent of the first formulation dissolve in the aqueous solution and start the disinfection of microorganisms adhering to the lens and the cleaning of protein adhering to the same. Thereafter, the foaming of the neutralizer of the second formulation starts after 1 to 10 minutes, and it can be observed visually that the solution and the soft contact lens colored yellow or brown and the soft contact lens are gradually discolored and become colorless eventually. Cleaning is continued during this procedure and completes in 1 to 600 minutes after the start of cleaning. The lens disinfected, neutralized and cleaned is rinsed using the aforementioned rinsing solution and put on eyes.

EXAMPLES

The following examples are given to further illustrate the present invention. However, it should be understood that the present invention is not limited by these examples.

Example 1

| Components | mg/formulation |
| --- | --- |
| The First Formulation (powder) | |
| Povidone iodine (iodine-based disinfectant) | 3 |
| Subtilisin A (proteolytic enzyme) | 6 |
| Lactose (excipient) | 91 |

| Components | mg/formulation |
| --- | --- |
| -continued | |
| The Second Formulation (tablet) | |
| Sodium hydrogen sulfite | 3 |
| Poloxamer (nonionic surfactant) | 5 |
| Sodium carbonate (foaming agent, pH adjustor) | 30 |
| Citric acid (pH adjustor) | 10 |
| Lactose (excipient) | 12 |
| HEC (coating) | 5 |

After a tablet was formed, it was coated with HEC.

| Aqueous Solution (liquid) | |
| --- | --- |
| Components | mg/ml |
| Sodium chloride (isotonicity) | 8 |
| EDTA·2Na (chelating agent) | 1 |
| Boric acid (buffer) | 5 |
| Borax (buffer) | 1 |
| Purified water (solvent) | proper quantity |

The above first formulation (powder) and the above second formulation (tablet) were packaged in an aluminum three-sealed-side package to prepare a one-solution type of combined formulation. The aqueous solution (liquid) was charged into a PE bottle.

Example 2

| Components | mg/formulation |
| --- | --- |
| The First Formulation (granule) | |
| Povidone iodine (iodine-based disinfectant) | 3 |
| Trypsin (proteolytic enzyme) | 3 |
| Polyoxyl 40 Stearate (nonionic surfactant) | 5 |
| Lactose (excipient) | 87 |
| The Second Formulation (tablet) | |
| Sodium sulfite (reducer) | 3 |
| Sodium carbonate (foaming agent, pH adjustor) | 30 |
| Citric acid (pH adjustor) | 10 |
| Lactose (excipient) | 12 |
| HPMC (coating) | 5 |

After a tablet was formed, it was coated with HPMC.

| Aqueous Solution (liquid) | |
| --- | --- |
| Components | mg/ml |
| Sodium chloride (isotonicity) | 7 |
| EDTA·2Na (chelating agent) | 1 |
| Monopotassium phosphate (buffer) | 1 |
| Disodium phosphate (buffer) | 1.5 |
| Purified water (solvent) | proper quantity |

The above first formulation (granule) and the above second formulation (tablet) were packaged in an aluminum three-sealed-side package to prepare a one-solution type of combined formulation. The aqueous solution (liquid) was charged into a PE bottle.

Example 3

| Components | mg/formulation |
|---|---|
| The First Formulation (powder) | |
| Povidone iodine (iodine-based disinfectant) | 3 |
| Trypsin (proteolytic enzyme) | 1 |
| Chymotrypsin (proteolytic enzyme) | 1 |
| Poloxamer (nonionic surfactant) | 5 |
| Lactose (excipient) | 90 |
| The Second Formulation (capsule) | |
| Sodium thiosulfate (reducer) | 2 |
| Sodium bicarbonate (foaming agent, pH adjustor) | 30 |
| Citric acid (pH adjustor) | 5 |
| Lactose (excipient) | 13 |
| Gelatin (encapsulating agent) | 5 |

After granules were prepared, they were charged into a gelatin capsule.

| Aqueous Solution (liquid) | |
|---|---|
| Components | mg/ml |
| Sodium chloride (isotonicity) | 6 |
| EDTA.2Na (chelating agent) | 1 |
| Boric acid (buffer) | 6 |
| Borax (buffer) | 1.5 |
| Purified water (solvent) | proper quantity |

The above first formulation (powder) and the above second formulation (capsule) were packaged in an aluminum three-sealed-side package to prepare a one-solution type of combined formulation. The aqueous solution (liquid) was charged into a PE bottle.

Comparative Example 1

| Components | mg/formulation |
|---|---|
| The First Formulation (powder) | |
| Povidone iodine (iodine-based disinfectant) | 3 |
| Papain (proteolytic enzyme) | 7 |
| Lactose (excipient) | 90 |
| The Second Formulation (tablet) | |
| Sodium hydrogen sulfite (reducer) | 3 |
| Poloxamer (nonionic surfactant) | 5 |
| Sodium carbonate (foaming agent, pH adjustor) | 30 |
| Citric acid (pH adjustor) | 10 |
| Lactose (excipient) | 12 |
| Aqueous Solution (liquid) | mg/ml |
| Sodium chloride (isotonicity) | 8 |
| EDTA.2Na (chelating agent) | 1 |
| Boric acid (buffer) | 5 |
| Borax (buffer) | 1 |
| Purified water (solvent) | proper quantity |

The above first formulation (powder) and the above second formulation (tablet) were packaged in a aluminum three-sealed-side-package to prepare a one-solution type of combined formulation. The aqueous solution (liquid) was charged into a PE bottle.

Example 4

The disinfection effects of the formulations prepared in Examples 1 to 3 and Comparative Example 1 were examined. The first and second formulations of each of Examples 1 to 3 and Comparative Example 1 were added at the same time to 10 ml of a solution prepared by adding microorganisms to each of the above aqueous solutions at a density of $10^6$ cfu/ml. After the second formulation was completely dissolved, 1 ml of the solution each was taken to a Petri dish to check the number of viable microorganisms. The results are shown in Table 1.

TABLE 1

| | Disinfection Effect Test (cfu/ml) | | | |
|---|---|---|---|---|
| Inoculated Microorganisms | Example 1 | Example 2 | Example 3 | Comparative Example 1 |
| S. aureus | 0 | 0 | 0 | $10^6$ |
| P. aeruginosa | 0 | 0 | 0 | $10^6$ |
| E. coli | 0 | 0 | 0 | $10^6$ |
| S. marcescens | 0 | 0 | 0 | $10^6$ |
| C. albicans | 0 | 0 | 0 | $10^6$ |
| A. niger | 0 | 0 | 0 | $10^6$ |

As is evident from Table 1, the disinfection effects of the formulations of Examples 1 to 3 are clearly observed. Since the second formulation of Comparative Example 1 did not have a delayed release coating, the disinfectant was immediately neutralized and the disinfection effect was not obtained at all.

Example 5

The cleaning effects of the formulations prepared in Examples 1 to 3 were examined. A HEMA lens was immersed in a 0.1% lysozyme solution and heated at 80° C. for 30 minutes to adhere thermally denatured lysozyme to the lens. This lens was scrubbed with a saline solution to obtain an artificially soiled lens. The artificially soiled lens was directly placed in each vial without fixation, 8 ml of each of the aqueous solutions prepared in Examples 1 to 3 was added to the vial, the first formulation and the second formulation were added into the vial, the lens was taken out from the vial after 4 hours, and the transmittances of the lens at 500 nm before and after staining and after treatment were measured. The removal rate of lysozyme was calculated from the following equation to check a cleaning effect.

$$\text{Removal Rate of Lysozyme } (\%) = (T2-T1)/(T0-T1) \times 100$$

T0: transmittance of lens before staining
T1: transmittance of lens after staining
T2: transmittance of lens after treatment The results are shown in Table 2.

TABLE 2

Cleaning Effect (removal rate of soiled, %)

| Number of Tests | Example 1 | Example 2 | Example 3 | Comparative Example 1 |
|---|---|---|---|---|
| 1 | 78.2 | 88.6 | 90.1 | 10.5 |
| 2 | 85.5 | 82.8 | 89.9 | 5.2 |
| 3 | 88.2 | 91.5 | 85.0 | 8.8 |
| Average Value | 84.0 | 87.5 | 88.3 | 8.2 |

As is evident from Table 2, the cleaning effects of the formulations of Examples 1 to 3 were observed. In Comparative Example 1, the proteolytic enzyme became deactivated and the cleaning effect was hardly observed.

Example 6

The safety of each formulation was tested using the eyes of house rabbits. Six HEMA lenses were fixed in respective vials and 8 ml of the aqueous solution prepared in Example 1 was added to each of the vials. Thereafter, the first formulation and the second formulation were added into each of the vials in the same manner and allowed to stand to carry out disinfection, neutralization and cleaning in one solution. After 4 hours, each lens was taken out, rinsed with the above aqueous solution and put on six eyes of house rabbits for 8 hours on the first day. On and after the second day, the same operation as described above was repeated for 5 days, and the eye irritancy of this system was evaluated every day. The evaluation was based on the observed score according to the criteria of Dratze (J. H. Draize, Association of Food and Drug Officials of the United States, Topeka, Kansas, pp.46, 1959) and on the corneal staining density with fluorescein immediately after removal of the lens from tested eyes on each day.

The Dratze score results of the safety test using the eyes of the house rabbits are shown in Table 3.

TABLE 3

| | Eye Number | | | | | |
|---|---|---|---|---|---|---|
| | 1 | 2 | 3 | 4 | 5 | 6 |
| | | | Date of Wearing | | | |
| Site | 12345 | 12345 | 12345 | 12345 | 12345 | 12345 |
| Cornea | | | | | | |
| (A) Opacity - Degress of Density | 00000 | 00000 | 00000 | 00000 | 00000 | 00000 |
| (B) Area of Opacity | 00000 | 00000 | 00000 | 00000 | 00000 | 00000 |
| Iris | | | | | | |
| (A) Values | 00000 | 00000 | 00000 | 00000 | 00000 | 00000 |
| Conjunctiva | | | | | | |
| (A) Redness | 10111 | 11100 | 11111 | 11111 | 10110 | 10011 |
| (B) Chemosis | 00000 | 00000 | 00000 | 00000 | 00000 | 00000 |
| (C) Discharge | 10000 | 10000 | 10000 | 11001 | 00000 | 10000 |
| Total Points | 40222 | 42200 | 42222 | 44224 | 20220 | 40022 |
| Staining of Cornea | All the test eyes were not stained. | | | | | |

Only slight redness and discharge were observed sporadically in contact lenses treated with the formulation prepared in Example 1 while they were worn, and no symptom suggesting corneal toxicity was obtained from the fluorescein staining test.

No lesion was observed on the formulations prepared in Examples 2 and 3 as well as the above result.

The criteria of the Draize method are shown in Table 4.

TABLE 4

| Site | Degree of Reaction | Evaluated Point |
|---|---|---|
| Cornea | (A) Opacity - Degree of Density | |
| | • Transparent, no opacity | 0 |
| | • Scattered or diffuse area, details of iris clearly visible | 1 |
| | • Easily discernible translucent areas, details of iris slightly obscured | 2 |
| | • Opalesent areas no details of iris visible, size of pupil barely discerible | 3 |
| | • Opaque, iris invisible | 4 |
| | (B) Area of Cornea | |
| | • 0~1/4 | 1 |
| | • 1/4~1/2 | 2 |
| | • 1/2~3/4 | 3 |
| | • 3/4~4/4 | 4 |
| Iris | (A) Values | |
| | • Normal | 0 |
| | • Folds above normal, congestion, swelling circumcorneal injection (any or all of these or combination of any thereof), iris still reacting to light sluggish reaction is positive) | 1 |
| | • No reaction to light, hemorrhage, gross destruction (any or all of these.) | 2 |
| Conjunctiva | (A) Redness of Palpebral and Bulbar Conjunctiva | |
| | • Vessels normal | 0 |
| | • Vessels definitely injected above normal | 1 |
| | • More diffuse, deeper crimson red, individual vessels not clearly discernible | 2 |
| | • Diffuse beefly red | 3 |
| | (B) Chemosis | |
| | • No swelling | 0 |
| | • Any swelling above normal (includes nictitating membrane) | 1 |
| | • Obvious swelling with partial eversion of lids | 2 |
| | • Swelling with lids about half closed | 3 |
| | • Swelling with lids about half closed to completely closed | 4 |
| | (C) Discharge | |
| | • No discharge | 0 |
| | • Any amount different from normal (does not include amount observed in inner thus of normal ) | 1 |
| | • Discharge with moistening of the lids and hairs just adjacent to lids | 2 |
| | • Discharge with moistening of the lids and hairs, and considerable area around the eye | 3 |

Evaluation points were determined by the symptoms and observations of the eye tissues and the safety of the formulation was evaluated by the total of these. Calculation of The Total of The evaluation points:

Total Points=[cornea:A×B×5+iris:A×5+conjunctiva:(A+B+C)×2]

Evaluation:

0 to 5 points: no irritating 5 to 15 points: slightly irritating 15 to 30 points: irritating 30 to 60 pints: moderately irritating 60 to 80 points: moderately to strongly irritating 80 to 110 points: strongly irritating According to the present invention, by simultaneously adding a formulation that contains an iodine-based disinfectant and a proteolytic enzyme and a formulation that contains a neutralizer treated with a delayed release coating and a surfactant into a vial that contains a soft contact lens and an aqueous solution, after bacteria adhering to the lens can be disinfected completely in a short period of time, the completion of neutralization can be confirmed visually because the aqueous solution and the lens colored by iodine became colorless by a neutralizer, and protein and lipid adhering to the lens can be cleaned automatically. Therefore, a series of lens cares, that is, disinfection, neutralization and cleaning can be carried out easily, efficiently and safely.

What is claimed is:

1. A one-solution type of combined formulation for disinfecting, neutralizing and cleaning a contact lens, which comprises:
   (A) a first formulation containing an iodine-based disinfectant as a sole disinfectant and a proteolytic enzyme, wherein said iodine-based disinfectant is a member selected from the group consisting of povidone iodine and polyvinyl alcohol iodine, and
   (B) a second formulation containing a reducer and a foaming agent and having a delayed release coating, said reducer reduces iodine molecules remaining in a soft contact lens after disinfection and is a member selected from the group consisting of sodium hydrogen sulfite, sodium sulfite, sodium thio sulfate, ascorbic acid and sodium ascorbate, and at least one of the first and the second formulations containing a nonionic surfactant.

2. The one-solution type of combined formulation of claim 1, wherein the iodine-based disinfectant is contained in an amount of 0.01 to 50 wt % based on the first formulation.

3. The one-solution type of combined formulation of claim 1, wherein the proteolytic enzyme of the first formulation is selected from the group consisting of enzymes derived from bacillus bacteria and enzymes derived from animal pancreases.

4. The one-solution type of combined formulation of claim 1, wherein the proteolytic enzyme is contained in an amount of 0.01 to 50 wt % based on the first formulation.

5. The one-solution type of combined formulation of claim 1, wherein the nonionic surfactant is selected from the group consisting of polyoxyethylene-polyoxypropylene block polymer, polyoxyethylene-polyoxypropylene block polymer of ethylene di-amine, polyoxyethylene 20 sorbitan monooleate, polyethylene glycol monostearate and polyoxyethylene hydrogenated castor oil 60.

6. The one-solution type of combined formulation of claim 1, wherein the iodine-based disinfectant of the first formulation is povidone iodine or polyvinyl alcohol iodine, the proteolytic enzyme is selected from enzymes derived from bacillus bacteria and enzymes derived from animal pancreases, and the nonionic surfactant of the first or the second formulation is selected from the group consisting of polyoxyethylene-polyoxypropylene block copolymer, polyoxyethylene-polyoxypropylene block copolymer of ethylene di-amine, polyoxyethylene 20 sorbitan monooleate, polyethylene glycol monostearate and polyoxyethylene hydrogenated castor oil 60.

7. The one-solution type of combined formulation of claim 1, wherein the reducer is contained in an amount of 0.01 to 50 wt % based on the second formulation.

8. The one-solution type of combined formulation of claim 1, wherein the foaming agent of the second formulation is selected from the group consisting of sodium bicarbonate and sodium carbonate.

9. The one-solution type of combined formulation of claim 1, wherein the foaming agent is contained in an amount of 1 to 80 wt% based on the second formulation.

10. The one-solution type of combined formulation of claim 1, wherein the delayed release coating of the second formulation is made from a compound selected from the group consisting of hydroxyethyl cellulose, hydroxypropyl cellulose, hydroxypropyl methyl cellulose and gelatin.

11. The one-solution type of combined formulation of claim 1, wherein the delayed release coating of the second formulation delays the release of the foaming agent by at least 1 to 10 minutes after the second formulation is injected into an aqueous solution.

12. The one-solution type of combined formulation of claim 1, wherein the reducer of the second formulation is selected from the group consisting of sodium hydrogen sulfite, sodium sulfite, sodium thiosulfate, ascorbic acid and sodium ascorbate, the foaming agent is selected from the group consisting of sodium bicarbonate and sodium carbonate, and the delayed release coating is made from a compound selected from the group consisting of hydroxyethyl cellulose, hydroxypropyl cellulose, hydroxypropyl methyl cellulose and gelatin.

13. The one-solution type of combined formulation of claim 1, wherein the weight ratio of the first formulation to the second formulation is in the range of 10/90 to 90/10.

14. The one-solution type of combined formulation of claim 1, wherein the first formulation is in a powdery or granular form and the second formulation is in a tablet or capsule form.

15. The one-solution type of combined formulation of claim 1, wherein the second formulation forms a center portion and the first formulation forms an outer layer covering the center portion.

16. The one-solution type of combined formulation of claim 1, wherein the proteolytic enzymes of the first formulation is selected from the group consisting of enzymes derived from bacillus bacteria and enzymes derived from animal pancreases, the foaming agent of the second formulation is selected from the group consisting of sodium bicarbonate and sodium carbonate, the delayed release coating of the second formulation is made from a compound selected from the group consisting of hydroxypropyl cellulose, hydroxypropyl methyl cellulose and gelatin, and the nonionic surfactant of each of the first and the second formulation is selected from the group consisting of polyoxyethylene-polyoxypropylene block polymer, polyoxyethylene-polyoxypropylene block polymer of ethylene diamine, polyoxyethylene 20 sorbitan monooleate, polyethylene glycol, monostearate and polyoxyethylene hydrogenated castor oil 60.

17. A method of disinfecting, neutralizing and cleaning a contact lens, which comprises the steps of:
   holding a soiled contact lens in a yellow or brown aqueous solution in which the first formulation (A) of the one-solution type of combined formulation of claim 1 is dissolved and
   removing the contact lens from the aqueous solution after the second formulation is dissolved in the aqueous solution and the aqueous solution becomes almost colorless.

18. The method of claim 17, wherein when the first and second formulations are added into the aqueous solution at the same time, the first formulation dissolves first to clean and disinfect the lens, and thereafter, the reducer and foaming agent of the second formulation substantially start to dissolve to neutralize the iodine-based disinfectant.

19. The method of claim 17, wherein the contact lens is removed from the aqueous solution 1 to 600 minutes after the aqueous solution becomes almost colorless by neutralization.

20. The method of claim 17, wherein the aqueous solution further contains at least one isotonicity selected from the group consisting of sodium chloride and potassium chloride.

21. The method of claim 17, wherein the aqueous solution further contains at least one buffer selected from the group consisting of phosphates, boric acid and borates.

22. The method of claim 17, wherein the aqueous solution further contains at least one chelating agent selected from the group consisting of ethylenediamine disodium tetraacetate and ethylenediamine dipotassium tetraacetate.

23. The method of claim 17, wherein the aqueous solution contains at least one isotonicity selected from the group consisting of sodium chloride and potassium chloride, at least one buffer selected from the group consisting of phosphates, boric acid and borates and at least one chelating agent selected from the group consisting of ethylenediamine disodium tetraacetate and ethylenediamine dipotassium tetraacetate.

24. A one-solution type of combined formulation for disinfecting, neutralizing and cleaning a soft contact lens, which comprises:

(A) a first formulation consisting essentially of an iodine-based disinfectant and a proteolytic enzyme, and (B) a second formulation consisting essentially of a reducer and a foaming agent and having a delayed release coating, at least one of the first and the second formulations contains a nonionic surfactant, wherein the iodine-based disinfectant of the first formulation is a member selected from the group consisting of povidone iodine and polyvinyl alcohol iodine and the proteolytic enzyme is a member selected from the group consisting of enzymes derived from bacillus bacteria and enzymes derived from animal pancreases, and wherein the nonionic surfactant is selected from the group consisting of polyoxyethylene-polyoxypropylene block polymer, polyoxyethylene-polyoxypropylene block polymer of ethylene di-amine, polyoxyethylene 20 sorbitan monooleate, polyethylene glycol monostearate and polyoxyethylene hydrogenated castor oil 60.

* * * * *